United States Patent
Valade

(10) Patent No.: US 12,358,890 B2
(45) Date of Patent: Jul. 15, 2025

(54) SUBSTITUTED TETRAHYDROISOQUINOLINE DERIVATIVE AS A D1 POSITIVE ALLOSTERIC MODULATOR

(71) Applicant: UCB Biopharma SRL, Brussels (BE)

(72) Inventor: Anne Valade, Brussels (BE)

(73) Assignee: UCB BIOPHARMA SRL, Brussels (BE)

( * ) Notice: Subject to any disclaimer, the term of this patent is extended or adjusted under 35 U.S.C. 154(b) by 740 days.

(21) Appl. No.: 17/621,871

(22) PCT Filed: Jun. 29, 2020

(86) PCT No.: PCT/EP2020/068181
§ 371 (c)(1),
(2) Date: Dec. 22, 2021

(87) PCT Pub. No.: WO2021/001286
PCT Pub. Date: Jan. 7, 2021

(65) Prior Publication Data
US 2022/0251064 A1    Aug. 11, 2022

(30) Foreign Application Priority Data
Jul. 1, 2019    (EP) .................... 19183641

(51) Int. Cl.
*C07D 401/06*    (2006.01)

(52) U.S. Cl.
CPC .................. *C07D 401/06* (2013.01)

(58) Field of Classification Search
None
See application file for complete search history.

(56) References Cited

FOREIGN PATENT DOCUMENTS

| | | |
|---|---|---|
| RU | 2610262 | 12/2015 |
| WO | 2013/066736 | 5/2013 |
| WO | 2016/055479 | 4/2016 |
| WO | 2017178377 | 10/2017 |

OTHER PUBLICATIONS

International Search Report dated Nov. 10, 2020 for International Application PCT/EP2020/068181.
Kümmerer, Klaus "Pharmaceuticals in the environment" Annual review of environment and resources (2010) vol. 35, pp. 57-75.
Wesserling, Martyna et al. "Will in vitro tests replace animal models in experimental oncology?", Journal of tissue science and engineering (2011) vol. 2(1), p. 102e. doi: 10.4172/2157-7552.1000102e.
Szajewska, H. "Evidence-based medicine and clinical research: both are needed, neither is perfect", Annals of nutrition and metabolism (2018) vol. 72(3), pp. 13-23.

*Primary Examiner* — Samantha L Shterengarts
(74) *Attorney, Agent, or Firm* — McDonnell Boehnen Hulbert & Berghoff LLP

(57) ABSTRACT

The present invention relates to compounds according to formula (I), which are a positive allosteric modulators of D1 and accordingly of benefit as pharmaceutical agents for the treatment of diseases in which D1 receptors play a role.

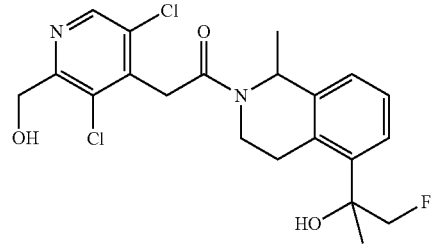

11 Claims, No Drawings

SUBSTITUTED TETRAHYDROISOQUINOLINE DERIVATIVE AS A D1 POSITIVE ALLOSTERIC MODULATOR

CROSS-REFERENCE TO RELATED APPLICATIONS

This application is a U.S. national phase of International Application No. PCT/EP2020/068181, filed Jun. 29, 2020, which claims priority from European Patent Application No. EP 19183641.0 filed Jul. 1, 2019, the disclosure of each of which is hereby incorporated by reference in its entirety.

The invention relates to a tetrahydroisoquinoline derivative and its use in therapy. In particular the present invention relates to a pharmacologically active substituted tetrahydroisoquinoline derivative.

This compound acts as a D1 Positive Allosteric Modulator and is accordingly of benefit as a pharmaceutical agent for the treatment of diseases in which D1 receptors play a role.

The monoamine dopamine acts via two families of GPCRs to modulate motor function, reward mechanisms, cognitive processes and other physiological functions. Specifically, dopamine is acting upon neurons via D1-like, comprising dopamine D1 and D5, receptors which couple mainly to the Gs G-protein and thereby stimulate cAMP production, and D2-like, which comprise D2, D3 and D4, receptors which couple to Gi/q G-proteins and which attenuate cAMP production. These receptors are widely expressed in different brain regions. In particular, D1 receptors are involved in numerous physiological functions and behavioural processes. D1 receptors are, for instance, involved in synaptic plasticity, cognitive function and goal-directed motor functions, but also in reward processes. Due to their role in several physiological/neurological processes, D1 receptors have been implicated in a variety of disorders including cognitive and negative symptoms in schizophrenia, cognitive impairment related to classical antipsychotic therapy, impulsivity, attention disorder with hyperactivity (ADHD), Parkinson's disease and related movement disorders, dystonia, Huntington's disease, dementia with Lewy Body, Alzheimer's disease, age-related cognitive decline, mild cognitive impairment (MCI), drug addiction sleep disorders, apathy.

It has proven difficult to develop orally-bioavailable small molecules targeting D1 receptors. D1 agonists developed so far are generally characterized by a catechol moiety and their clinical use has therefore been limited to invasive therapies. Achieving sufficient selectivity has also been challenging due to the high degree of homology in the ligand binding site between dopamine receptors subtypes (e.g. dopamine D1 and D5). Also, D1 agonists are associated with potentially limiting side effects including but not limited to dyskinesia and hypotension.

There is therefore a need to design new agents that could modulate D1 receptors.

There has been much interest in the identification of allosteric modulators of GPCRs, both as tools to understand receptor mechanisms and as potential therapeutic agents. GPCRs represent the largest family of cell-surface receptors and a large number of marketed drugs directly activate or block signaling pathways mediated by these receptors. However, for some GPCRs (e.g. peptide receptors), it has proven challenging to develop small molecules or to achieve sufficient selectivity due to the high degree of homology in the ligand binding site between subtypes (e.g. dopamine D1 and D5 or D2 and D3). Accordingly, much drug research has shifted to the identification of small molecules which target sites distinct from the orthosteric natural agonist. Ligands which bind to these sites induce a conformational change in the GPCR thereby allosterically modulating the receptor function. Allosteric ligands have a diverse range of activities including the ability to potentiate (positive allosteric modulator, PAM) or attenuate (negative allosteric modulator, NAM) the effects of the endogenous ligand, by affecting affinity and/or efficacy. As well as subtype selectivity, allosteric modulators may present other potential advantages from a drug discovery perspective such as a lack of direct effect or intrinsic efficacy; only potentiating the effect of the native transmitter where and when it is released; reduced propensity for inducing desensitization arising from constant exposure to an agonist as well as reduced propensity to induce target-related side-effects.

The compounds according to the present invention potentiates the effect of D1 agonists or of the endogenous ligand on D1 receptors through an allosteric mechanism, and is therefore a D1 Positive Allosteric Modulator (D1 PAM).

The compound in accordance with the present invention, being a D1 PAM, is therefore beneficial in the treatment and/or prevention of diseases and disorders in which D1 receptors play a role. Such diseases include cognitive and negative symptoms in schizophrenia, cognitive impairment related to neuroleptic therapy, Mild cognitive impairment (MCI), impulsivity, Attention-Deficit Hyperactivity Disorder (ADHD), Parkinson's disease and other movement disorders, dystonia, Parkinson's dementia, Huntington's disease, dementia with Lewy Body, Alzheimer's disease, drug addiction, sleep disorders, apathy, traumatic spinal cord injury or neuropathic pain.

International patent application WO 2013/051869 A1 discloses certain 3,4-dihydro-1H-isoquinolin-2-yl derivatives which are NK2 antagonists.

International patent application WO2008/109336 A1 discloses certain tetrahydroisoquinoline compounds which are modulators of the histamine H3 receptors.

International patent application WO2014/193781 A1 discloses certain 3,4-dihydroisoquinolin-2(1H)-yl derivatives useful for the treatment of cognitive impairment associated with Parkinson's disease or Schizophrenia.

International patent application WO2016/055479 discloses substituted 3,4-dihydroisoquinolin-2(1H)-yl derivatives and analogs thereof which may be useful for the treatment of diseases in which D1 receptors play a role.

International patent application WO2019/204418 discloses certain pyrazo-tetrahydroisoquinolines derivatives which are D1 positive allosteric modulators and may be useful in the treatment of Parkinson's disease and other movement disorders, Alzheimer's disease, Schizophrenia, and Attentiondeficit hyperactivity disorder (ADHD).

However, there remains a need to develop potent D1 positive allosteric modulators combining advantageous pharmacokinetic and pharmacodynamic properties while reducing side effects traditionally associated with treatments involving selective D1 agonists, such as for example movement or cognitive disorders.

The present invention provides 2-[3,5-dichloro-2-(hydroxymethyl)-4-pyridyl]-1-[5-[2-fluoro-1-hydroxy-1-methyl-ethyl]-1-methyl-3,4-dihydro-1H-isoquinolin-2-yl] ethenone of formula (I),

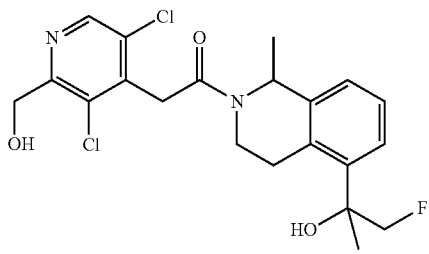

(I)

or a pharmaceutically acceptable salt thereof.

The compound according to the present invention is encompassed within the generic scope of co-pending international patent application WO2016/055479. There is, however, no specific disclosure therein of the compound of formula (I) as depicted above, or a pharmaceutically acceptable salt thereof.

The present invention also provides a compound of formula (I) as defined above or a pharmaceutically acceptable salt thereof, for use in therapy.

In another aspect, the present invention also provides a compound of formula (I) as defined above, or a pharmaceutically acceptable salt thereof, for use in the treatment and/or prevention of diseases and/or disorders in which D1 receptors play a role.

In another aspect, the present invention provides a compound of formula (I) as defined above, or a pharmaceutically acceptable salt thereof, for use in the treatment and/or prevention of cognitive and negative symptoms in schizophrenia, cognitive impairment related to neuroleptic therapy, Mild Cognitive impairment (MCI), impulsivity, Attention-Defficit Hyperactivity Disorder (ADHD), Parkinson's disease and other movement disorders, dystonia, Parkinson's dementia, Huntington's disease, dementia with Lewy Body, Alzheimer's disease drug addiction, sleep disorders, apathy, traumatic spinal cord injury or neuropathic pain.

In a particular embodiment of this aspect, the present invention provides a compound of formula (I) as defined above, or a pharmaceutically acceptable salt thereof for use in the treatment of Parkinson's disease and other movement disorders, Alzheimer's disease, or cognitive and negative symptoms in schizophrenia.

Therefore, in one particular aspect, the present invention provides a compound of formula (I), as defined above, or a pharmaceutically acceptable salt thereof, for use in the treatment of Parkinson's disease and other movement disorders.

In a further aspect, the present invention provides for the use of a compound of formula (I) as defined above, or a pharmaceutically acceptable salt thereof, for the manufacture of a medicament useful for the treatment and/or prevention of diseases and/or disorders in which D1 receptors play a role.

In another further aspect, the present invention provides for the use of a compound of formula (I) as defined above, or a pharmaceutically acceptable salt thereof, for the manufacture of a medicament useful for the treatment and/or prevention of cognitive and negative symptoms in schizophrenia, cognitive impairment related to neuroleptic therapy, Mild Cognitive Impairment (MCI), impulsivity, Attention-Deficit HyperactivityDisorder (ADHD), Parkinson's disease and other movement disorders, dystonia, Parkinson's dementia, Huntington's disease, dementia with Lewy Body, Alzheimer's disease, drug addiction, sleep disorders, apathy, traumatic spinal cord injury or neuropathic pain.

In a particular embodiment of this aspect, the present invention provides for the use of a compound of formula (I) as defined above, or a pharmaceutically acceptable salt thereof for the manufacture of a medicament useful for the treatment of Parkinson's disease and other movement disorders, Alzheimer's disease, or cognitive and negative symptoms in schizophrenia.

In one particular aspect, the present invention provides for the use of a compound of formula (I), as defined above, or a pharmaceutically acceptable salt thereof, for the manufacture of a medicament useful for the treatment of Parkinson's disease and other movement disorders.

The present invention also provides a method for the treatment and/or prevention of disorders for which the administration of D1 positive allosteric modulator is indicated, which comprises administering to a patient in need of such treatment an effective amount of a compound of formula (I) as defined above, or a pharmaceutically acceptable salt thereof.

In another aspect, the present invention provides a method for the treatment and/or prevention of cognitive and negative symptoms in schizophrenia, cognitive impairment related to neuroleptic therapy, Mild Cognitive Impairment (MCI), impulsivity, Attention-Deficit Hyperactivity Disorder (ADHD), Parkinson's disease and other movement disorders, dystonia, Parkinson's dementia, Huntington's disease, dementia with Lewy Body, Alzheimer's disease, drug addiction, sleep disorders, apathy, traumatic spinal cord injury or neuropathic pain, which comprises administering to a patient in need of such treatment an effective amount of a compound of formula (I) as defined above, or a pharmaceutically acceptable salt thereof.

In a particular embodiment of this aspect, the present invention provides a method for the treatment of Parkinson's disease and other movement disorders, Alzheimer's disease, or cognitive and negative symptoms in schizophrenia, which comprises administering to a patient in need of such treatment of an effective amount of a compound of formula (I) as defined above, or a pharmaceutically acceptable salt thereof.

In one particular aspect, the present invention provides a method for the treatment of Parkinson's disease and other movement disorders, which comprises administering to a patient in need of such treatment of an effective amount of a compound of formula (I) as defined above, or a pharmaceutically acceptable salt thereof.

For use in medicine, the salts of the compound of formula (I) will be pharmaceutically acceptable salts. Other salts may, however, be useful in the preparation of the compound of formula (I) or of its pharmaceutically acceptable salts. Standard principles underlying the selection and preparation of pharmaceutically acceptable salts are described, for example, in *Handbook of Pharmaceutical Salts: Properties, Selection and Use*, ed. P. H. Stahl & C. G. Wermuth, Wiley-VCH, 2002. Suitable pharmaceutically acceptable salts of the compound of formula (I) include acid addition salts which may, for example, be formed by mixing a solution of the compound of formula (I) with a solution of a pharmaceutically acceptable acid.

It is to be understood that each individual atom present in formula (I), or in the formulae depicted hereinafter, may in fact be present in the form of any of its naturally occurring isotopes, with the most abundant isotope(s) being preferred. Thus, by way of example, each individual hydrogen atom present in formula (I), or in the formulae depicted hereinafter, may be present as a $^1H$, $^2H$ (deuterium) or $^3H$ (tritium) atom, preferably $^1H$. Similarly, by way of example, each individual carbon atom present in formula (I), or in the formulae depicted hereinafter, may be present as a $^{12}C$, $^{13}C$ or $^{14}C$ atom, preferably $^{12}C$.

The present invention includes within its scope solvates of the compounds of formula (I) above. Such solvates may be formed with common organic solvents or water.

The present invention also includes within its scope co-crystals of the compounds of formula (I) above. The technical term "co-crystal" is used to describe the situation where neutral molecular components are present within a crystalline compound in a definite stoichiometric ratio. The preparation of pharmaceutical co-crystals enables modifications to be made to the crystalline form of an active pharmaceutical ingredient, which in turn can alter its physicochemical properties without compromising its intended biological activity (see *Pharmaceutical Salts and Co-crystals*, ed. J. Wouters & L. Quere, RSC Publishing, 2012).

Compounds according to the present invention may exist in different polymorphic forms. Although not explicitly indicated in the above formula, such forms are intended to be included within the scope of the present invention.

The invention also includes within its scope pro-drug forms of the compounds of formula (I) and its various sub-scopes and sub-groups.

Compound of formula (I) contains 2 asymmetric centres and thus may accordingly exist as diastereomers. The invention is to be understood to extend to the use of all such diastereisomers, and to mixtures thereof in any proportion. Formula (I) is therefore intended to represent all individual stereoisomers and all possible mixtures thereof, unless stated or shown otherwise.

A particular aspect of the present invention provides 2-[3,5-dichloro-2-(hydroxymethyl)-4-pyridyl]-1-[(1S)-5-[(1S)-2-fluoro-1-hydroxy-1-methyl-ethyl]-1-methyl-3,4-dihydro-1H-isoquinolin-2-yl]ethenone of formula (IA),

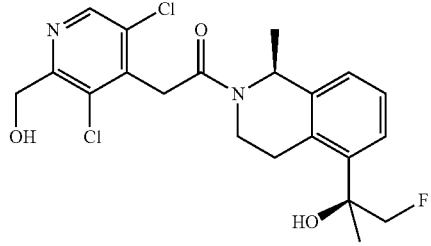

(IA)

or a pharmaceutically acceptable salt thereof.

Activity in any of the above-mentioned therapeutic indications or disorders can of course be determined by carrying out suitable clinical trials in a manner known to a person skilled in the relevant art for the particular indication and/or in the design of clinical trials in general.

For treating diseases, compound of formula (I) or its pharmaceutically acceptable salts may be employed at an effective daily dosage and administered in the form of a pharmaceutical composition.

Therefore, the present invention also provides a pharmaceutical composition comprising the compound of formula (I) as depicted above, or a pharmaceutically acceptable salt thereof, in association with one or more pharmaceutically acceptable carriers.

To prepare a pharmaceutical composition according to the invention, one or more of the compounds of formula (I) or a pharmaceutically acceptable salt thereof is intimately admixed with a pharmaceutical diluent or carrier according to conventional pharmaceutical compounding techniques known to the skilled practitioner.

Suitable diluents and carriers may take a wide variety of forms depending on the desired route of administration, e.g., oral, rectal, parenteral or intranasal.

Pharmaceutical compositions according to the present invention can, for example, be administered orally, parenterally, i.e., intravenously, intramuscularly or subcutaneously, intrathecally, by inhalation or intranasally.

Pharmaceutical compositions suitable for oral administration can be solids or liquids and can, for example, be in the form of tablets, pills, dragees, gelatin capsules, solutions, syrups, chewing-gums and the like.

To this end the active ingredient may be mixed with an inert diluent or a non-toxic pharmaceutically acceptable carrier such as starch or lactose. Optionally, these pharmaceutical compositions can also contain a binder such as microcrystalline cellulose, gum tragacanth or gelatine, a disintegrant such as alginic acid, a lubricant such as magnesium stearate, a glidant such as colloidal silicon dioxide, a sweetener such as sucrose or saccharin, or colouring agents or a flavouring agent such as peppermint or methyl salicylate.

The invention also contemplates compositions which can release the active substance in a controlled manner. Pharmaceutical compositions which can be used for parenteral administration are in conventional form such as aqueous or oily solutions or suspensions generally contained in ampoules, disposable syringes, glass or plastics vials or infusion containers.

In addition to the active ingredient, these solutions or suspensions can optionally also contain a sterile diluent such as water for injection, a physiological saline solution, oils, polyethylene glycols, glycerine, propylene glycol or other synthetic solvents, antibacterial agents such as benzyl alcohol, antioxidants such as ascorbic acid or sodium bisulphite, chelating agents such as ethylene diamine-tetra-acetic acid, buffers such as acetates, citrates or phosphates and agents for adjusting the osmolarity, such as sodium chloride or dextrose.

These pharmaceutical forms are prepared using methods which are routinely used by pharmacists.

The quantity of a compound of use in the invention required for the prophylaxis or treatment of a particular condition will vary depending on the compound chosen and the condition of the patient to be treated. In general, however, the daily dosage may range from 0.05 to 3000 mg, typically from 0.5 mg to 1000 mg for parenteral compositions.

The compound in accordance with the present invention, or a pharmaceutically acceptable salt thereof may be administered alone (monotherapy) or in combination with L-dopa (combination therapy). Alone or in combination with fractions of the L-dopa doses necessary to ameliorate motor disability in patients, the compounds of formula (I) according to the present invention, or pharmaceutical acceptable salts thereof, may be useful for the treatment of dyskinesia associated with administration of L-dopa. For example, if a compound of formula (I) in accordance with the present invention is used with fractions of the L-dopa doses given to patient or used alone to replace L-dopa, it is believed that compound of formula (I) according to the present invention will be effective against motor disability without inducing troublesome dyskinesia. Therefore it is believed that the compound according to the present invention may be useful for the treatment of motor deficits and levodopa-induced dyskinesia (LID).

Therefore, in one particular aspect, the present invention also provides a compound of formula (I), which is useful for the treatment of levodopa induced dyskinesia (LID).

The compound in accordance with the present invention, or a pharmaceutically acceptable salt thereof may be administered alone or in combination with another pharmaceutically active ingredient.

Compound of formula (I) may be prepared by a process involving reacting an intermediate of formula (II) with an intermediate of formula (III),

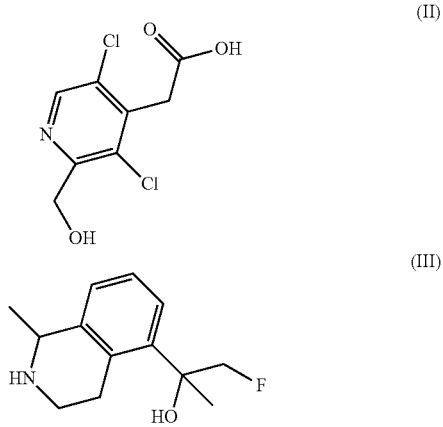

The hydrochloride salt of intermediate (III) is then reacted with intermediate of formula (II) in the presence of (2-(1H-benzotriazol-1-yl)-1,1,3,3-tetramethyluronium hexafluorophosphate (HBTU) or another coupling agent known to the person skilled in the art, in a suitable solvent, e.g. dimethylformamide, with an excess of a base, e.g. N,N-diisopropylethylamine.

Intermediates of formula (III) may be prepared by a process involving reaction of an intermediate of formula (IV) wherein Y represents halogen, e.g. bromo, with commercially available fluoroacetone.

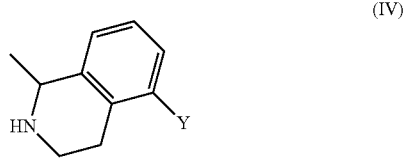

The reaction is conveniently effected by metal-halogen exchange e.g. in the presence of n-BuLi, in a suitable solvent, e.g. tetrahydrofuran, at low temperature, according to methods known to the skilled person in the art.

In the above reactions, the amino group of intermediates of formula (III) and (IV) will generally first be protected with an appropriate protective group, e.g. tert-butoxycarbonyl group, according to methods know to the skilled in the art, before being reacted with further reagents.

Intermediates of formula (IIIa) may be prepared by a process involving reaction of an intermediate of formula (V),

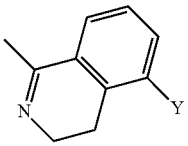

wherein Y is as defined here above.

The reaction is conveniently effected in the presence of a suitable reducing agent, e.g. sodium borohydride, in a suitable solvent, e.g. ethanol, at low temperature, according to methods known to the skilled person in the art.

Intermediates of formula (V) may be prepared by a process involving reaction of an intermediate of formula (VI),

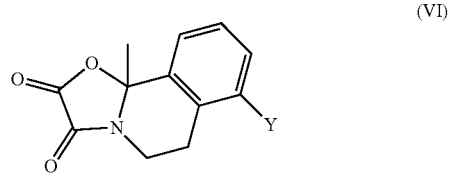

wherein Y is as defined here above.

The reaction is conveniently effected in the presence of sulfuric acid in a suitable solvent, e.g. methanol, at room temperature.

Intermediate of formula (VI) may be prepared by a process involving reaction of commercially available intermediate (VII),

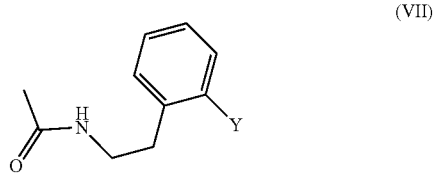

wherein Y is as defined here above.

The reaction is conveniently effected in the presence of oxalyl chloride, in a suitable solvent, e.g. dichloromethane, at low temperature, followed by the addition of ferric chloride at room temperature.

Intermediate of formula (II) may be prepared by a multi-step process involving reaction of intermediates represented by formula (VIII),

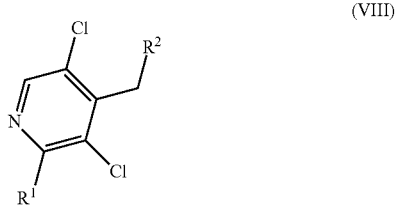

wherein
$R^1$ represents hydrogen, —$CH_2OH$, —$COOR^a$ or Y as defined above;

$R^2$ represents —COOR$^a$; and

R$^a$ represents hydrogen or C$_{1-6}$ alkyl.

In a first step, intermediate of formula (VIII) wherein R$^1$ represents hydrogen and R$^a$ represents a methyl is reacted with an oxidizing agent, e.g. m-chloroperbenzoic acid (m-CPBA) at low temperature, in a suitable solvent, e.g. dichloromethane, to afford the corresponding N-oxide.

In a second step, the N-oxide obtained as a result of the first step, is reacted with phosphorus oxybromide to afford corresponding intermediate of formula (VIII) wherein R$^1$ represents Y as defined here above, and R$^a$ represents a methyl.

In a third step, intermediate of formula (VIII) wherein R$^1$ represents Y as defined here above, is reacted with carbon monoxide in the presence of a base, e.g. N,N-diisopropylethylamine, in the presence of a transition metal catalyst, e.g. 1,4-bis(diphenylphosphino)butane-palladium (II) chloride, to afford corresponding intermediate of formula (VIII) wherein R$^1$ represents —COOR$^a$, and R$^a$ represents methyl. The reaction is conveniently effected at high pressure and at high temperature.

The ester group in R$^1$ of the latter intermediate is subsequently reduced into the corresponding alcohol, followed by hydrolysis of the ester group in R$^2$ into the corresponding carboxylic acid, to afford intermediate of formula (II). The reaction is effected according to methods well known to the person skilled in the art and as further specified in the accompanying Examples.

Intermediate of formula (VIII) wherein R$^1$ represents hydrogen and R$^a$ represents a methyl, may be prepared to methods analogous to those described in the accompanying examples or standard methods known to the person skilled in the art.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques. In particular, where it is desired to obtain a particular enantiomer of a compound of formula (I) this may be produced from a corresponding mixture of enantiomers using any suitable conventional procedure for resolving enantiomers. Thus, for example, diastereomeric derivatives, e.g. salts, may be produced by reaction of a mixture of enantiomers of formula (I), e.g. a racemate, and an appropriate chiral compound, e.g. a chiral base. The diastereomers may then be separated by any convenient means, for example by crystallisation, and the desired enantiomer recovered, e.g. by treatment with an acid in the instance where the diastereomer is a salt. In another resolution process a racemate of formula (I) may be separated using chiral HPLC. Moreover, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode. Chromatography, recrystallisation and other conventional separation procedures may also be used with intermediates or final products where it is desired to obtain a particular geometric isomer of the invention. Alternatively the non desired enantiomer may be racemized into the desired enantiomer, in the presence of an acid or a base, according to methods known to the person skilled in the art, or according to methods described in the accompanying Examples.

During any of the above synthetic sequences it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 3rd edition, 1999. The protecting groups may be removed at any convenient subsequent stage utilising methods known from the art.

The compounds of formula (I) according to the present invention do not directly activate the dopamine D1 receptor, but potentiate the effect of D1 agonists or the endogenous ligand on D1 receptors, dopamine, through an allosteric mechanism, and are therefore D1 positive allosteric modulator (D1 PAM).

Dopamine and other D1 agonists directly activate the dopamine D1 receptor by themselves.

Assays have been designed to measure the effects of compounds in accordance with the present invention in the absence of dopamine ("activation assay") and in the presence of dopamine ("potentiation assay").

The activation assay measures the stimulation of the production of cyclic adenosinemonophosphate (cAMP) in the Homogeneous Time Resolved Fluorescent (HTRF) assay, with the maximum increase in cAMP by increasing concentrations of the endogenous agonist, dopamine, defined as 100% activation.

When tested, compounds of formula (I) according to the Examples lack significant direct agonist-like effects in that they produce less than about 20% of activation (compared to dopamine maximal response) when present in a concentration of 10 µM.

The potentiation assay measures the ability of compounds to increase the levels of cAMP produced by a low-threshold concentration of dopamine. The concentration of dopamine used ([EC20]) is designed to produce 20% stimulation compared to the maximal response (100%) seen with increasing the concentration of dopamine. To measure this potentiation increasing concentrations of the compound with the [EC20] of dopamine are incubated and the potentiation is measured as increases in cAMP production and concentration of compound which produces 50% of the potentiation of the cAMP levels is measured.

When tested in the cAMP HTRF assay, compounds of formula (I) according to the Examples have exhibited values of pEC50 of greater than about 6.5 which shows that they are D1 Positive Allosteric Modulators.

GABA$_A$ receptor inhibition is known to be intimately linked to seizures and epilepsy. It is therefore desirable to develop compounds which are D1 Positive Allosteric Modulators and which at the same time minimize such effects.

When tested in a GABA-A receptor inhibition assay as described herein, compounds of formula (I) have displayed a percentage of inhibition of the GABA$_A$ receptor of less than or equal to about 20% measured at a concentration of 10 µM of a compound of formula (I).

A problem which can be faced when developing compounds for use in therapy is the capacity for certain compounds to inhibit CYP450 enzymes. The inhibition of such enzymes may impact the exposure of such compounds or of other compounds which could be co-administered therewith to a patient, thereby potentially altering their respective safety or efficacy. It is therefore desirable to develop compounds which minimize such potential for inhibition.

The CYP450 inhibition potential of compound of formula (I) according to the present invention has been tested by measuring the potential decrease of CYP450 activities in human hepatocytes incubated with increasing concentrations of compounds according to the present invention.

When tested in the CYP3A4 inhibition assay at 1 and 20 µM concentration according to the protocol described in the present patent application, compound of formula (I) according to the present invention exhibits an inhibition of less than about 40%, ideally less than about 30%.

When developing a compound for use in therapy, it is important to have an idea of its elimination once it has been administrated into the body.

The clearance is a parameter which gives that information because it represents the volume of plasma (or blood) totally cleaned from the compound of interest by time unit. It is usually expressed as ml/min/kg or L/h. It can then be compared to any physiological blood flow (e.g. liver blood flow) to evaluate if the clearance is low, moderate or high.

When clearance is low, depending on the volume of distribution, one might expect to need a low dose and to get a relatively long duration of action. When clearance is high, again depending on the volume of distribution, one might expect to need a high dose and to get a relatively short duration of action.

The clearance is generally evaluated by using hepatocyte incubations and scaling calculations, assuming the main elimination pathway is metabolism, according to protocols described herein. The intrinsic clearance evaluated from hepatocytes is expressed in $\mu l/min/10^6$ cells.

When tested in the clearance assay as described herein, the compound of formula (I) in accordance with the present invention advantageously exhibit a clearance of less than about 10 $\mu l/min/10^6$ cells.

cAMP HTRF Assay

The particular conditions in which the compounds have been tested are described here below.

a. METHODS D1 Cell Culture

Cells were cultured at 37° C. in a humidified atmosphere of 5% $CO_2$. Cells were grown in DMEM-F12+GlutaMAX™-I medium (GIBCO®, Invitrogen, Merelbeke, Belgium) containing 10% fetal bovine serum (BioWhittaker®, Lonza, Verviers, Belgium), 400 µg/mL Geneticin (GIBCO®), 100 IU/mL Penicillin and 100 IU/mL Streptomycin (Pen-Strep solution, BioWhittaker®). LMtk (Ltk-) mouse fibroblast cells expressing the dopamine D1 receptor (BioSignal Inc, Montreal, Canada, now Perkin Elmer) were used as they have been shown to couple efficiently and give robust functional responses (Watts et al, 1995).

b. cAMP Assay

The measurement of changes in intracellular cyclic adenosinemonophopshpate (cAMP) was determined using the HTRF cAMP dynamic assay kit from CisBio (Codolet, France). Using homogenous time-resolved fluoresence technology, the assay is based on competition between native cAMP produced by cells and cAMP labelled with the dye d2. The tracer binding is determined by an anti-cAMP antibody labeled with cryptate. The effects of the compound alone (agonism) was determined by performing the assay in the absence of dopamine, whilst the effect of the compound as a positive allosteric modulator (PAM) was determined in the presence of an $EC_{20}$ concentration of dopamine. Cells (20, 000 per well) are incubated in 384 plates for 1 hour at room temperature in a final volume of 20 µL HBSS (Lonza, with calcium, magnesium and HEPES buffer 20 mM, pH 7.4) containing: isobutyl methylxanthine (Sigma, 0.1 mM final), varying concentrations of test compound (typically $10^{-9.5}$M to $10^{-4.5}$M) in the presence and absence of dopamine (1.1 nM final). The reaction is then terminated and the cells lysed by adding the d2 detection reagent in lysis buffer (10 microL) and the cryptate reagent in lysis buffer (10 microl) according to manufacturer's instructions. This is then incubated for a further 60 min at room temperature and changes in HTRF fluorescent emission ratio determined according to manufacturer's instructions using an Envision plate reader (Perkin Elmer, Zaventem, Belgium) with laser excitation. All incubations were performed in duplicate and results were compared to a concentration-effect curve to dopamine. ($10^{-11}$M to $10^{-6}$M).

c. Data Analysis

Data was analyzed using Excel and PRISM (GraphPad Software) to obtain $pEC_{50}$ and Erel using the 4-parameter logistic equation (DeLean et al, 1978) where Erel is the fitted maximal response of the test compound minus basal expressed as a percentage relative to that obtained with dopamine which was defined as 100%.

The $pEC_{50}$ of a compound is the −log 10 of the concentration of the compound which produces 50% of the potentiation of the cAMP levels.

The Erel is the relative efficacy, defined as the maximal % potentiation produced by the compound compared to the maximal response produced by increasing concentrations of dopamine (Erel of 1=dopamine maximum response).

When tested in the present assay, compound of formula (Ia) exhibits a value of pEC50 of about 6.9 and compound of formula (Ib) exhibits a value of pEC50 of about 6.7.

The corresponding Erel exhibited by compound of formula (Ia) is about 64% and the corresponding Erel exhibited by compound of formula (Ib) is about 61%.

Automated Patch Clamp Studies on the $GABA_A$ Receptor Cells

CHO-K1 cells stably expressing human $GABA_A$ receptor $\alpha1, \beta2$ and $\gamma2$ subunits were used. The cells were harvested using trypsin and maintained in serum-free medium at room temperature. The cells were washed and re-suspended in extracellular solution before testing.

Patch Clamp Studies

Experiments on human $GABA_A$ ($\alpha_1\beta_2\gamma_2$) channels were conducted using an automated patch clamp assay (IonFlux™ HT). Compounds were tested at 3 concentrations (0.1, 1, and 10 µM) in 3 to 4 cells. The external solution for recording $GABA_A$ currents was composed of sodium chloride 137 mM, potassium chloride 4 mM, calcium chloride 1.8 mM, magnesium chloride 1 mM, HEPES 10 mM, and glucose 10 mM. Both external and internal solutions were titrated with NaOH or KOH to obtain a pH of 7.35 or 7.3, respectively. The internal pipette solution contained potassium fluoride 70 mM, potassium chloride 60 mM, sodium chloride 70 mM, HEPES 5 mM, EGTA 5 mM, and Magnesium ATP 4 mM. The final concentration of vehicle used to dilute compounds was 0.33% DMSO in each well. Bicuculline (0.032 to 100 µM) was used as positive control inhibitor. GABA (15 µM) was used as agonist. All recordings were obtained from a holding potential of −60 mV.

The compound addition sequence was the following: one addition of the $EC_{80}$ concentration of GABA was added to establish baseline response. Each concentration of compound was applied for 30 seconds followed by the addition of 15 µM GABA in the presence of the compound for 2 seconds. The process was repeated with the next ascending concentration of compound. Peak inward currents in response to the GABA additions in the presence of a single concentration of compound were measured. All compound data have been normalized to the baseline peak current induced by addition of 15 µM GABA for 2 seconds.

When tested in the above mentioned assay, at a concentration of 10 µM, compound of formula (Ia) exhibits a percentage of inhibition of the $GABA_A$ receptor of about 13%.

When tested in the above mentioned assay, at a concentration of 10 µM, compound of formula (Ib) exhibits a percentage of inhibition of the $GABA_A$ receptor of about 20%.

In Vitro Assessment of CYP3A4 Inhibition Potential Using Cryopreserved Human Microsomes The objective of the human microsome assay is to characterize the inhibition potential of Compound of formula (I) by measuring the CYP3A4 activities after its co-incubation with midazolam, a specific CYP3A4 substrate.

To this aim, cryopreserved human microsomes (pooled donors) are divided on a 48 well collagen coated plate so that the final concentration is 0.25 mg/ml. The UCB compound is then added in the wells at 1 µM and 20 µM concentration in duplicate. After 30 minutes incubation, midazolam is added at 2.5 µM concentration. After 15 minutes, an aliquot is removed and placed into an equal volume of methanol containing internal standard. The samples are centrifuged at 2500 rpm at 4° C. for 20 min. An aliquot of supernatant is diluted with deionised water and levels of 1-hydroxymidazolam is quantified using generic LC MS/MS methods.

The concentrations are compared to those obtained after midazolam incubation at the same concentration but without UCB compound pre-incubation. The results are expressed as % of inhibition.

Compound of formula (Ia) according to the present invention exhibits a percentage of inhibition of CYP3A4 of about 28% at a concentration of 20 µM and of about 20% at a concentration of 1 µM.

Azamulin Assay

Cryopreserved human hepatocytes (pool of 20 donors, BSU batch from Celsis/IVT/Bioreclamation) were thawed accordingly the provider's information. Viability (trypan blue exclusion) was higher than 75%. Pre-incubations (250 µL of hepatocytes suspension at $2 \times 10^6$ hepatocytes/mL) were carried out with William's medium, containing 2 mM of glutamine and 15 mM of Hepes, in 48-well plates at +37° C., in an incubator (5% $CO_2$), under gentle agitation (vibrating agitator, Titramax 100, ca 300 rpm) during 30 min. After the pre-incubation, the incubation was initiated by adding to hepatocytes, 250 µL of culture medium (see composition above) containing UCB compound (1 µM) or midazolam (positive control). Final concentrations of UCB compound in the incubates are 0.5 µM. The cell suspensions was rapidly re-homogenized by 2 in-out pipetting. After 0, 30, 60, 120, 180 and 240 minutes of incubation, reactions were stopped by transferring 50 µl of incubates into the appropriate well from 96-well plate containing 50 µL of ice cold acetonitrile with ketoconazole 1 µM as internal standard. Before each sampling, cell incubates are re-homogenized by 2 in out pipetting.

Samples are analyzed by LC-MS-MS bioanalytical method to measure the concentration of UCB compound. The concentration versus time profile is fitted to determine the intrinsic clearance (Clint) expressed as $\mu l/min/10^6$ cells.

When incubated with human hepatocyte suspension at different concentrations the intrinsic clearance (Clint) of compound of formula (Ia) according to the present invention is equal to about 8.8 $\mu l/min/10^6$ cells and the intrinsic clearance (Clint) of compound of formula (Ib) is about 9.2 $\mu l/min/10^6$ cells.

The following Examples illustrates the preparation of compounds of formula (I) according to the present invention.

EXAMPLES

Abbreviations/Recurrent Reagents

ACN: Acetonitrile
cAMP: cyclic adenosinemonophosphate
Brine: Saturated aqueous sodium chloride solution
nBu: n-butyl
tBu: tert-butyl
CHO: Chinese hamster ovary
m-CPBA: 3-chloroperbenzoic acid
CYP450: Cytochromes P450
DCM: Dichloromethane
DMF: N,N-Dimethylformamide
DMSO: Dimethylsulfoxide
$EC_{20/50}$: concentration which produces 20%/50% of the maximum response
EGTA: Egtazic acid
Erel: relative efficacy
$ES^+$: Electrospray Positive Ionisation
Et: Ethyl
EtOH: Ethanol
$Et_2O$: Diethyl ether
EtOAc: Ethyl acetate
GABA: γ-aminobutyric acid
h: Hour
HEPES: 4-(2-Hydroxyethyl)-1-piperazineethanesulfonic acid
HPLC: High Pressure Liquid Chromatography
HTRF: homogenous time-resolved fluorescence
LCMS: Liquid Chromatography Mass Spectrometry
LDA: Lithium diisopropylamide
MeOH: Methanol
min.: minutes
NMR: Nuclear magnetic resonance
iPrOH: isopropanol
rt: room temperature
SFC: Supercritical Fluid Chromatography
TEA: Triethylamine
THF: Tetrahydrofuran
TLC: Thin Layer Chromatography
IUPAC names have been determined using Biovia Draw 16.1.

Analytical Methods

All reactions involving air or moisture-sensitive reagents were performed under a nitrogen or argon atmosphere using dried solvents and glassware. Commercial solvents and reagents were generally used without further purification, including anhydrous solvents when appropriate (generally Sure-Seal™ products from Aldrich Chemical Company or AcroSeal™ from ACROS Organics). In general reactions were followed by thin layer chromatography, HPLC or mass spectrometry analyses.

HPLC analyses are performed using an Agilent 1100 series HPLC system mounted with a Waters XBridge MS C18, 5 pm, 150×4. 6 mm column. The gradient runs from 100% solvent A (water/ACN/ammonium formate solution 85/5/10 (v/v/v)) to 100% solvent B (water/ACN/ammonium formate solution 5/85/10 (v/v/v) in 6 min. with a hold at 100% B of 5 minutes. The flow rate is set at 8 mL/min during 6 min. then increased at 3 mL/min during 2 min. with a hold at 3 mL/min during 3 minutes. A split of 1/25 is used just before API source. The chromatography is carried out at 45° C. The ammonium formate solution (pH~8.5) is prepared by dissolution of ammonium formate (630 mg) in water (1 L) and addition of ammonium hydroxide 30% (500 µL).

It will be apparent to the one skilled in the art that different retention times may be obtained for LC data if different analytical conditions are used.

Mass spectrometric measurements in LCMS mode are performed as follows:

For basic elution, analyses are performed using:

A QDA Waters simple quadrupole mass spectrometer is used for LCMS analysis. This spectrometer is equipped with an ESI source and an UPLC Acquity Hclass with diode array detector (200 to 400 nm). Data are acquired in a full MS scan from m/z 70 to 800 in positive mode with a basic elution. The reverse phase separation is carried out at 45° C. on a Waters Acquity UPLC BEHC18 1.7 µm (2.1×50 mm) column for basic elution. Gradient elution is done with water/ACN/ammonium formate (95/5/63 mg/L) (solvent A) and ACN/water/ammonium formate (95/5/63 mg/L) (solvent B). Injection volume: 1 µL. Full flow in MS.

Basic Program "4 Min"

| Time (min) | A (%) | B (%) | Flow (mL/min) |
|---|---|---|---|
| 0 | 99 | 1 | 0.4 |
| 0.3 | 99 | 1 | 0.4 |
| 3.2 | 0 | 100 | 0.4 |
| 3.25 | 0 | 100 | 0.5 |
| 4 | 0 | 100 | 0.5 |

Basic Program "10 Min"

| Time (min) | A (%) | B (%) | Flow (mL/min) |
|---|---|---|---|
| 0 | 99 | 1 | 0.4 |
| 0.8 | 99 | 1 | 0.4 |
| 5.3 | 0 | 100 | 0.4 |
| 5.35 | 0 | 100 | 0.5 |
| 7.30 | 0 | 100 | 0.5 |

For acidic elution, analyses are performed using:

A QDA Waters simple quadrupole mass spectrometer is used for LCMS analysis. This spectrometer is equipped with an ESI source and an UPLC Acquity Hclass with diode array detector (200 to 400 nm). Data are acquired in a full MS scan from m/z 70 to 800 in positive mode with an acidic elution. The reverse phase separation is carried out at 45° C. on a Waters Acquity UPLC HSS T3 1.8 µm (2.1×50 mm) column for acidic elution. Gradient elution is done with water/ACN/TFA (95/5/0.5 mL/L) (solvent A) and ACN (solvent B). Injection volume: 1 µL. Full flow in MS.

Acidic Program "4 Min"

| Time (min) | A (%) | B (%) | Flow (mL/min) |
|---|---|---|---|
| 0 | 99 | 1 | 0.4 |
| 0.3 | 99 | 1 | 0.4 |
| 3.2 | 5 | 95 | 0.4 |
| 3.25 | 5 | 95 | 0.5 |
| 4 | 5 | 95 | 0.5 |

Acidic Program "10 Min"

| Time (min) | A (%) | B (%) | Flow (mL/min) |
|---|---|---|---|
| 0 | 99 | 1 | 0.4 |
| 0.8 | 99 | 1 | 0.4 |
| 5.3 | 5 | 95 | 0.4 |
| 5.35 | 5 | 95 | 0.5 |
| 7.30 | 5 | 95 | 0.5 |

Crude materials could be purified by normal phase chromatography, (acidic or basic) reverse phase chromatography, chiral separation or recrystallization.

Normal reverse phase chromatography are performed using silica gel columns (100:200 mesh silica gel or Puriflash®-50SIHC-JP columns from Interchim).

Preparative reverse phase chromatography are performed as follows:

LCMS purification (Basic mode, LCMS prep) using a SQD or QM Waters triple quadrupole mass spectrometer is used for LCMS purification. This spectrometer is equipped with an ESI source and a Prep LC controller Waters quaternary pump with diode array detector (210 to 400 nm).

MS parameters: ESI capillary voltage 3 kV. Cone and Extractor voltage 10. Source block temperature 120° C. Desolvation temperature 300° C. Cone gaz flow 30 L/h (Nitrogen), Desolvation Gas flow 650 L/h. Data are acquired in a full MS scan from m/z 100 to 700 in positive mode with an acidic or a basic elution.

LC parameters: The reverse phase separation is carried out at rt on a XBridge prep OBD C18 column (5 µm, 30×50 mm) (basic elution). Gradient elution is done with Water (solvent A), ACN (solvent B), Ammonium bicarbonate in water 8 g/L+500 µL/L NH$_4$OH 30% (solvent C) (pH~8.5). HPLC flow rate: 35 mL/min to 60 mL/min, injection volume: 1 mL. The splitting ratio is set at +/−1/6000 to MS.

| Time (min) | A (%) | B (%) | C (%) | Flow (mL/min) |
|---|---|---|---|---|
| 0 | 85 | 5 | 10 | 35 |
| 1 | 85 | 5 | 10 | 35 |
| 7 | 5 | 85 | 10 | 35 |
| 9 | 5 | 95 | 0 | 60 |
| 12 | 5 | 95 | 0 | 60 |
| 12.5 | 85 | 5 | 10 | 35 |
| 16 | 85 | 5 | 10 | 35 |

Crude materials could be purified by normal phase chromatography, (acidic or basic) reverse phase chromatography, chiral separation or recrystallization.

Products were generally dried under vacuum before final analyses and submission to biological testing.

All NMR spectra were obtained at 250 MHz, 300 MHz, 400 MHz or 500 MHz.

1. Preparation of Intermediate (II)— 2-[3,5-dichloro-2-(hydroxymethyl)-4-pyridyl]acetic acid

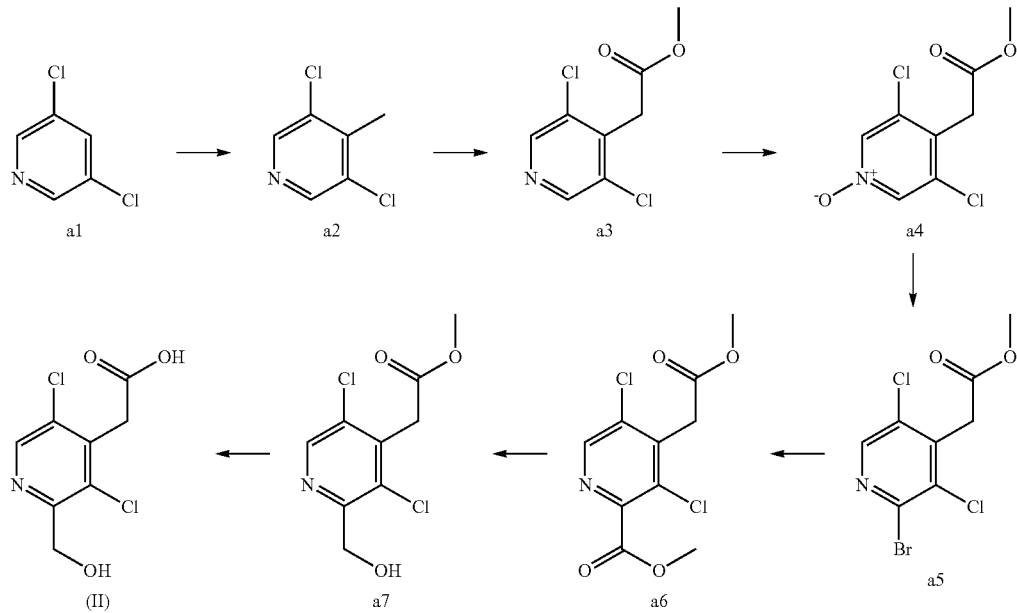

1.1. Preparation of 3,5-dichloro-4-methyl-pyridine a2

LDA (1.86 L, 2M solution in THF, 3.72 mol) and THF (5.0 L) are charged in a reactor under nitrogen. 3,5-Dichloro-4-methyl-pyridine a1 (500 g, 3.38 mol) is added at −20° C. and the mixture is stirred at −10° C. for 30 min. The reaction was cooled down to −70° C. and methyl iodide (815 g, 5.74 mol) is added. The mixture is allowed to warm to room temperature and is stirred for 4 h. This overall procedure is carried out on 4 batches of the same size in parallel which are worked up together. The mixture is cooled to 0° C. and quenched with water (5 L) and stirred for 10 min. The aqueous phase is extracted with ethyl acetate (2×3 L) and the combined organic phase are washed twice with brine (10 L), dried with anhydrous sodium sulfate, filtered and concentrated under vacuum. The crude product is purified by recrystallization from ethanol (4 L) at −70° C. to give 3,5-dichloro-4-methyl-pyridine a2 as a yellow solid (1.5 kg, 68.5% yield).

1.2. Preparation of methyl 2-(3,5-dichloro-4-pyridyl)acetate—Intermediate a3

3,5-Dichloro-4-methyl-pyridine a2 (375 g, 2.31 mol) and DMF (1.87 L) are charged in a reactor and the mixture is cooled down to 15° C. Potassium tert-butoxide (779 g, 6.94 mol) is added under nitrogen at 10-15° C. and the mixture is stirred at 15° C. for 30 min. Dimethyl carbonate (730 g, 8.10 mol) is added at 10-15° C. and the mixture is stirred for 4 h at 30° C. This overall procedure is carried out on 4 batches of the same size in parallel which are worked up together. The mixture is cooled to 0° C. and the reaction quenched with water (10 L) and stirred for 10 min. The reaction mixture is filtered and the filter cake is washed twice with ethyl acetate (2 L). The aqueous phase is extracted twice with ethyl acetate (3 L) and the combined organic phase is washed twice with brine (5 L), dried with anhydrous sodium sulfate, filtered and concentrated under vacuum to give methyl 2-(3,5-dichloro-4-pyridyl)acetate a3 as a black brown liquid (1.3 kg, 63.8% yield) which is used in the next step without further purification.

1.3. Preparation of methyl 2-(3,5-dichloro-1-oxido-pyridin-1-ium-4-yl)acetate—Intermediate a4

Methyl 2-(3,5-dichloro-4-pyridyl)acetate a3 (650 g, 2.95 mol) and dichloromethane (3.25 L) are charged in a reactor. m-CPBA (1.27 kg, 5.91 mol, 80% purity) is added at 0° C. under nitrogen and the mixture is stirred at 25° C. for 5 h. This overall procedure is carried out on two batches of the same size in parallel which are worked up together. The mixture is cooled to 0° C. and the reaction quenched with water (4 L) and stirred for 10 min. The reaction mixture is filtered and the filter cake is washed twice with dichloromethane (3 L). The aqueous phase is extracted twice with dichloromethane (2 L) and the combined organic phase is washed three times with a saturated solution of $Na_2S_2O_3$ (15 L) and twice with brine (10 L) then dried over anhydrous sodium sulfate, filtered and concentrated under vacuum. The residue is purified by silica gel chromatography (petroleum ether:ethyl acetate 20:1 to 1:1) to give methyl 2-(3,5-dichloro-1-oxido-pyridin-1-ium-4-yl)acetate a4 as a yellow solid (900 g, 64.2% yield).

1.4. Preparation of methyl 2-(2-bromo-3,5-dichloro-4-pyridyl)acetate—Intermediate a5

Methyl 2-(3,5-dichloro-1-oxido-pyridin-1-ium-4-yl)acetate a4 (900 g, 3.81 mol) and acetonitrile (8 L) are charged in a reactor at 20° C. Phosphorus oxybromide ($POBr_3$, 1.09 kg, 3.81 mol) is added at 0° C. under nitrogen and the mixture is stirred at 25° C. for 12 h. This overall procedure is carried out on another batch (1.64 mol scale) in parallel and the two are worked up together. The mixture is cooled to 0° C. and the reaction quenched with water (3 L) and stirred for 10 min. The aqueous phase is extracted twice with ethyl acetate (2 L). The combined organic phase is washed twice with brine (5 L), dried with anhydrous sodium sulfate, filtered and concentrated under vacuum. The residue is purified by silica gel chromatography (petroleum ether: ethyl acetate 50:1 to 1:1) to give methyl 2-(2-bromo-3,5-dichloro-4-pyridyl)acetate a5 as an off-white solid (503 g, 43% yield).
$^1$H NMR (400 MHz, CDCl$_3$) δ 8.32 (s, 1H), 4.07 (s, 2H), 3.75 (s, 3H)

1.5. Preparation of methyl 3,5-dichloro-4-(2-methoxy-2-oxo-ethyl)pyridine-2-carboxylate—Intermediate a6

To a solution of methyl 2-(2-bromo-3,5-dichloro-4-pyridyl)acetate a5 (3 g, 10.03 mmol) in methanol (60 mL) was added N,N-diisopropylethylamine (2.42 mL, 14.6 mmol) and 1,4-bis(diphenylphosphino)butane-palladium (II) chloride (91 mg, 0.15 mmol). The reactor was flushed three times with nitrogen then pressurized (3 flushes) with 5 bars of carbon monoxide and the mixture was heated at 80° C. for 3 hours. The reaction mixture was filtered at room temperature over celite and the solvent was removed under reduced pressure. The crude product was purified by column chromatography. (Biotage SNAP Ultra 25 g. Eluant:ethyl acetate:hexane 1:1). The solvent was removed under vacuum to yield 3,5-dichloro-4-(2-methoxy-2-oxo-ethyl)pyridine-2-carboxylate a6 as a yellow liquid (1.84 g, 66% yield).
LCMS (MH$^+$): 278
$^1$H NMR (400 MHz, DMSO-d$_6$) δ 8.75 (s, 1H), 4.12 (s, 2H), 3.93 (s, 3H), 3.68 (s, 3H).

1.6. Preparation of methyl 2-[3,5-dichloro-2-(hydroxymethyl)-4-pyridyl]acetate—Intermediate a7

To a solution of methyl 3,5-dichloro-4-(2-methoxy-2-oxo-ethyl)pyridine-2-carboxylate a6 (305 mg, 1.09 mmol) in THF (10 mL) was added at room temperature sodium borohydride (124 mg, 3.29 mmol) and the reaction mixture was allowed to stir at room temperature for 18 hours. The reaction mixture was filtered and the solvent was removed under vacuum. The crude product was purified by column chromatography (Biotage SNAP Ultra 25 g. Eluant:dichloromethane:methanol 100:0 to 90:10). The solvent was removed under vacuum to yield methyl 2-[3,5-dichloro-2-(hydroxymethyl)-4-pyridyl]acetate a7 as a solid (139 mg, 50% yield).
LCMS (MH$^+$): 250
$^1$H NMR (400 MHz, CDCl$_3$) δ 8.51 (s, 1H), 4.78 (s, 2H), 4.04 (s, 2H), 3.74 (s, 3H). OH proton not observed.

1.7. Preparation of Intermediate (II)— 2-[3,5-dichloro-2-(hydroxymethyl)-4-pyridyl]acetic acid To a solution of methyl 2-[3,5-dichloro-2-(hydroxymethyl)-4-pyridyl]acetate a7 (98.1 g, 392 mmol) in a mixture of THF (1.1 L) and water (110 mL) was added lithium hydroxide monohydrate (25.2 g, 589 mmol). The resulting mixture was stirred at room temperature for 18 hours before it was concentrated under vacuum. The residue was azeotropically co-evaporated with toluene (3×250 mL) to yield 2-[3,5-dichloro-2-(hydroxymethyl)-4-pyridyl]acetic acid (II) as a free-flowing off-white powder (92.6 g, 100% yield). The product was used in the next step without further purification.

$^1$H NMR (400 MHz, DMSO-d$_6$) δ 8.54 (s, 1H), 4.62 (s, 2H), 2.46 (s, 2H). Two OH protons were not seen.

2. Preparation of Intermediate (III)

Preparation of (1R)-1-fluoro-2-[(1S)-1-methyl-1,2,3,4-tetrahydroisoquinolin-5-yl]propan-2-ol hydrochloride a14-(R,S) and (1S)-1-fluoro-2-[(1S)-1-methyl-1,2,3,4-tetrahydroisoquinolin-5-yl]propan-2-ol hydrochloride a14-(S,S)

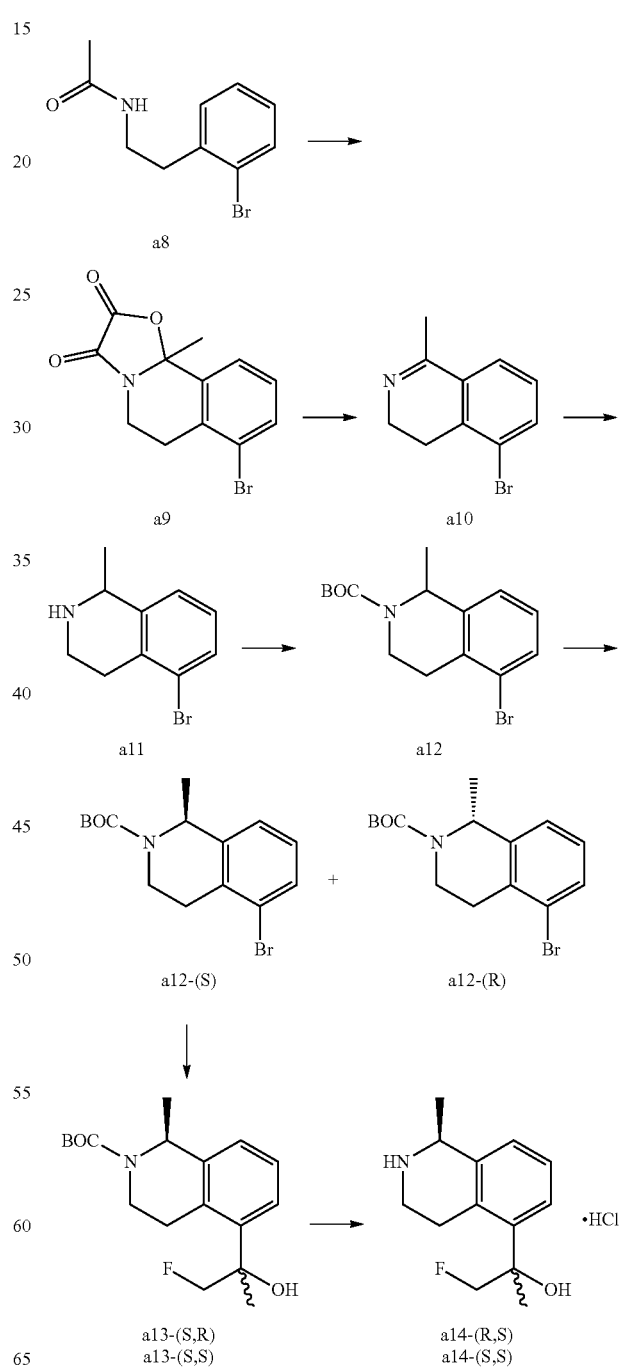

2.1. Preparation of Intermediate (VI)-7-bromo-10b-methyl-6,10b-dihydro-5H-[1,3]oxazolo[2,3-a]isoquinoline-2,3-dione a9

To a solution of N-[2-(2-bromophenyl)ethyl]acetamide a8 (commercial, 106.5 g, 439.8 mmol) in DCM (1.5 L) was added dropwise at 0° C. oxalyl chloride (72 mL, 838.7 mmol). The mixture was stirred at 0° C. for 2 h, then allowed to warm to rt and stirred for 3 h. The reaction mixture was then cooled to 0° C. and ferric chloride (86 g, 530.2 mmol) was added in 2 portions. The reaction mixture was allowed to warm to rt, stirred overnight at rt, diluted with DCM (2.5 L) and then quenched at 0° C. with a 12M concentrated solution of ammonia (200 mL). The organic layer was dried over $Na_2SO_4$, filtered and concentrated under vacuum to yield 108 g of 7-bromo-10b-methyl-6,10b-dihydro-5H-[1,3]oxazolo[2,3-a]isoquinoline-2,3-dione a9 as a brown solid, which was used in next step without any further purification.
Yield(crude): 83%.
LCMS (ES+): 296/298 (M+H)+.

2.2. Preparation of Intermediate (V)-5-bromo-1-methyl-3,4-dihydroisoquinoline a10

To a suspension of 7-bromo-10b-methyl-6,10b-dihydro-5H-[1,3]oxazolo[2,3-a]isoquinoline-2,3-dione a9 (108 g, 364.72 mmol) in MeOH (1.5 L) was added dropwise at rt sulfuric acid (75 mL). The reaction mixture was stirred overnight at 65° C., then quenched at 0° C. with a 15M concentrated solution of ammonia (300 mL). The mixture was concentrated under vacuum and water (300 mL) was added. The aqueous layer was extracted 6 times with DCM (1 L). The organic layer was dried over $MgSO_4$, filtered and concentrated under vacuum to afford 86.44 g of 5-bromo-1-methyl-3,4-dihydroisoquinoline a10 as a brown solid, which was used in next step without any further purification.
Yield (crude): quantitative.
HPLC (Basic Mode): RT 4.75 min, 87% purity.

2.3. Preparation of Intermediate (IV)-5-bromo-1-methyl-1,2,3,4-tetrahydroisoquinoline a11

To a solution of 5-bromo-1-methyl-3,4-dihydroisoquinoline a10 (86.44 g, 385.9 mmol) in EtOH (2 L) was added at 0° C. sodium borohydride (13.2 g, 349 mmol) portionwise (13*1 g). The mixture was stirred at 0° C. for 2 h, then a 5N aqueous solution of HCl solution (250 mL) was added at 0° C. The reaction mixture was stirred overnight at rt, then EtOH was concentrated under vacuum. DCM (1 L) was added and the mixture was quenched at 0° C. with a 6M concentrated solution of ammonia (400 mL). The organic layer was extracted twice with DCM (500 mL), dried over $MgSO_4$, filtered and concentrated under vacuum to afford 83 g of 5-bromo-1-methyl-1,2,3,4-tetrahydroisoquinoline a11 as a brown solid, which was used in next step without any further purification.
Yield (crude): 95%.
HPLC (Basic Mode): RT 4.53 min, 80% purity.

2.4. Preparation of tert-butyl 5-bromo-1-methyl-3,4-dihydroisoquinoline-2(1H)-carboxylate—Intermediates a12, a12-S and a12-R To a solution of 5-bromo-1-methyl-1,2,3,4-tetrahydroisoquinoline a11 (78 g, 345 mmol) in DCM (1 L) was added TEA (160 mL, 1136 mmol) at 0° C. A solution of di-tert-butyl dicarbonate (65 g, 294.8 mmol) in DCM (250 mL) was then added dropwise at 0° C. The reaction mixture was stirred overnight at rt and quenched with water (100 mL). The organic layer was dried over $MgSO_4$, filtered and concentrated under vacuum. The residue was triturated twice in a mixture of MeOH/n-hexanes (1:2, 450 mL) to yield 63 g of tert-butyl 5-bromo-1-methyl-3,4-dihydroisoquinoline-2(1H)-carboxylate a12 (Yield: 56%, HPLC (Basic Mode): RT 6.59 min, 98% purity) as a white solid.
Chiral separation (SFC, Whelko 01(R,R), 50*227 mm, 360 mL/min, 220 nm, 25° C., eluent: from 20% iPrOH) of racemate tert-butyl 5-bromo-1-methyl-3,4-dihydroisoquinoline-2(1H)-carboxylate a12 afforded:
  25.1 g of tert-butyl (1S)-5-bromo-1-methyl-3,4-dihydroisoquinoline-2(1H)-carboxylate a12-S as a solid.
Yield: 22%.
HPLC (Basic Mode): RT 6.59 min, 91% purity.
Chiral analysis (LC, Whelko-01 (R,R), 250*4.6 mm, 1 mL/min, 220 nm, 30° C., eluent: iPrOH/n-heptane/DEA 50/50/0.1) RT 4.86 min, 97.7% ee.
  29.3 g of tert-butyl (1R)-5-bromo-1-methyl-3,4-dihydroisoquinoline-2(1H)-carboxylate a12-R as a solid.
Yield: 26%.
HPLC (Basic Mode): RT 6.59 min, 98% purity.
Chiral analysis (LC, Whelko-01 (R,R), 250*4.6 mm, 1 mL/min, 220 nm, 30° C., eluent: iPrOH/n-heptane/DEA 50/50/0.1) RT 5.62 min, 92.4% ee.

2.5. Preparation of tert-butyl (1S)-5-[(1R)-2-fluoro-1-hydroxy-1-methyl-ethyl]-1-methyl-3,4-dihydro-1H-isoquinoline-2-carboxylate intermediate a13-(S,R) and tert-butyl (1S)-5-[(1S)-2-fluoro-1-hydroxy-1-methyl-ethyl]-1-methyl-3,4-dihydro-1H-isoquinoline-2-carboxylate—intermediate a13-(S,S)

tert-Butyl (1S)-5-bromo-1-methyl-3,4-dihydro-1H-isoquinoline-2-carboxylate a12-S (7 g, 21.45 mmol) was dissolved in dry tetrahydrofuran (107 mL) at −78° C. n-BuLi (32.93 mmol) was added dropwise and the mixture was stirred at −78° C. for 10 min. Fluoroacetone (4.78 mL, 64.2 mmol) was added and the mixture was stirred at rt for 1 h. The reaction mixture was quenched with a 1N aqueous solution of HCl (350 mL), then extracted three times with dichloromethane. The organic layer was dried over $MgSO_4$, filtered and concentrated under vacuum. The residue was purified by reverse phase chromatography (basic mode, standard LC). Chiral separation (LC, chiralpak IC, 80*380 mm, 300 mL/min, 220 nm, 30° C., eluent: 10% iPrOH in heptane) afforded:
  1.137 g of tert-butyl (1S)-5-[(1R)-2-fluoro-1-hydroxy-1-methyl-ethyl]-1-methyl-3,4-dihydro-1H-isoquinoline-2-carboxylate a13-(S,R) as a beige solid.
Yield: 16%
LCMS (ES+): 268.0 (M-tBu+H)+.
Chiral analysis (LC, Whelko-01 (R,R), 150*4.6 mm, 1.5 mL/min, 220 nm, 30° C., eluent: iPrOH/n-heptane/DEA 10/90/0.1): RT 2.37 min, 100% ee.
  1.074 g of tert-butyl (1S)-5-[(1S)-2-fluoro-1-hydroxy-1-methyl-ethyl]-1-methyl-3,4-dihydro-1H-isoquinoline-2-carboxylate a13-(S,S) as a beige solid.
Yield: 15%
LCMS (ES+): 268.0 (M-tBu+H)+.
Chiral analysis (LC, Whelko-01 (R,R), 150*4.6 mm, 1.5 mL/min, 220 nm, 30° C., eluent: iPrOH/n-heptane/DEA 10/90/0.1): RT 2.72 min, 100% ee.

2.6. Preparation of (1R)-1-fluoro-2-[(1S)-1-methyl-1,2,3,4-tetrahydroisoquinolin-5-yl]propan-2-ol hydrochloride a14-(R,S) and (1S)-1-fluoro-2-[(1S)-1-methyl-1,2,3,4-tetrahydroisoquinolin-5-yl]propan-2-ol hydrochloride—Intermediate a14-(S,S)

tert-Butyl (1S)-5-[(1R)-2-fluoro-1-hydroxy-1-methyl-ethyl]-1-methyl-3,4-dihydro-1H-isoquinoline-2-carboxylate a13-(S,R) (1.137 g, 3.516 mmol) was dissolved in dioxane (18 mL) at rt. A 4N solution of HCl in dioxane (8.8 mL, 35 mmol) was added. The mixture was stirred at rt overnight. The reaction mixture was concentrated under vacuum to yield 950 mg of (1R)-1-fluoro-2-[(1S)-1-methyl-1,2,3,4-tetrahydroisoquinolin-5-yl]propan-2-ol hydrochloride a14-(R,S) as a beige solid.
Yield (crude): quantitative.
LCMS (ES+): 224.0 (M+H)+.

(1S)-1-fluoro-2-[(1S)-1-methyl-1,2,3,4-tetrahydroisoquinolin-5-yl]propan-2-ol hydrochloride a14-(S,S)

Compound a14-(S,S) may be synthetized according to the same method using tert-butyl (1S)-5-[(1S)-2-fluoro-1-hydroxy-1-methyl-ethyl]-1-methyl-3,4-dihydro-1H-isoquinoline-2-carboxylate a13-(S,S) as starting material.
Yield(crude): quantitative.
LCMS (ES+): 224 (M+H)+.

3. Preparation of Compound of Formula (I)

3.1. Preparation of Compound of Formula (Ia)—2-[3,5-dichloro-2-(hydroxymethyl)-4-pyridyl]-1-[(1S)-5-[(1S)-2-fluoro-1-hydroxy-1-methyl-ethyl]-1-methyl-3,4-dihydro-1H-isoquinolin-2-yl]ethanone

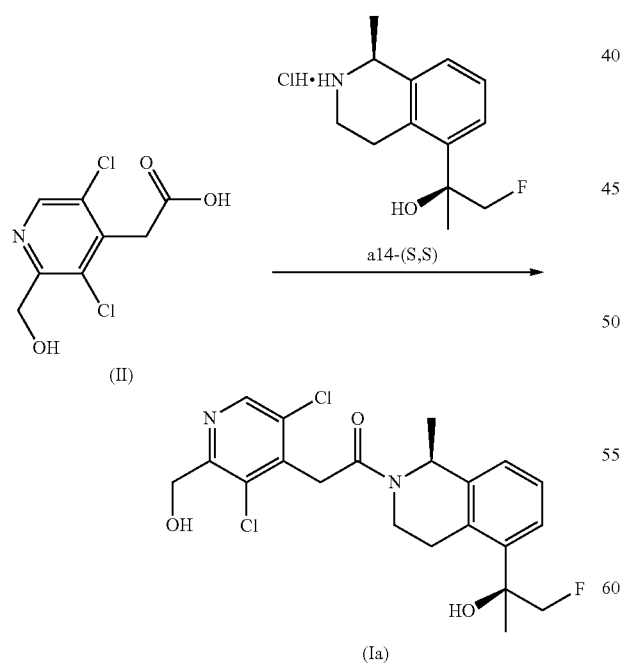

To a solution of 2-[3,5-dichloro-2-(hydroxymethyl)-4-pyridyl]acetic acid A (112 mg, 0.476 mmol) and (2S)-1-fluoro-2-[(1S)-1-methyl-1,2,3,4-tetrahydroisoquinolin-5-yl]propan-2-ol hydrochloride a14-(S,S) (136 mg, 0.524 mmol) in DMF (6 mL) was added (2-(1H-benzotriazol-1-yl)-1,1,3,3-tetramethyluronium hexafluorophosphate (HBTU, 217 mg, 0.571 mmol). Then, N,N-diisopropylethylamine (0.24 mL, 1.43 mmol) was added at room temperature and the mixture was stirred for 2 hours. The reaction mixture was quenched with water and extracted twice with ethyl acetate. The combined organic layers were dried over MgSO$_4$, filtered and the solvent was removed under vacuum to give the crude product. The crude product was purified by reverse phase chromatography (Basic Mode) and the solvent was removed under vacuum to yield 2-[3,5-dichloro-2-(hydroxymethyl)-4-pyridyl]-1-[(1S)-5-[(1S)-2-fluoro-1-hydroxy-1-methyl-ethyl]-1-methyl-3,4-dihydro-1H-isoquinolin-2-yl]ethanone 1 (116 mg, 55% yield) as a solid.
LCMS: 441 (MH+)
$^1$H NMR (400 MHz, DMSO-d$_6$) δ 8.59 (2 s, 1H, rotamers), 7.37-7.09 (m, 3H), 5.48 (m, 1H), 5.34 (m, 2H), 4.72-4.53 (m, 3H), 4.53-4.25 (m, 1.3H), 4.25-4.03 (m, 1.7H), 4.02-3.69 (m, 2H), 3.48 (m, 0.7H), 3.38-3.33 (m, 0.3H partially under water signal), 3.31-3.07 (m, 1H), 1.60 (d, J=6.7 Hz, 1H), 1.53 (m, 3H), 1.37 (d, J=6.7 Hz, 2H).

3.2. Preparation of Compound of Formula (Ib) of 2-[3,5-dichloro-2-(hydroxymethyl)-4-pyridyl]-1-[(1S)-5-[(1R)-2-fluoro-1-hydroxy-1-methyl-ethyl]-1-methyl-3,4-dihydro-1H-isoquinolin-2-yl]ethanone Title compound was prepared according to a procedure analogous to the one described for compound of formula (Ia) starting from (2S)-1-fluoro-2-[(1R)-1-methyl-1,2,3,4-tetrahydroisoquinolin-5-yl]propan-2-ol hydrochloride a14-(S,R).
LCMS: 441 (MH+)
$^1$H NMR (400 MHz, DMSO-d$_6$) δ 8.58 (2 s, 1H, 2 rotamers), 7.42-7.07 (m, 4H), 5.47 (s, 1H, rotamers), 5.41-5.24 (m, 2H), 4.85-4.66 (m, 1H), 4.57-4.24 (m, 2H), 4.09 (s, 3H), 4.01-3.70 (m, 2H), 3.58-3.19 (m, 1H partially under water signal), 1.59 (d, J=6.7 Hz, 1H), 1.53 (m, 3H), 1.36 (dd, J=6.8, 2.0 Hz, 2H).

The invention claimed is:
1. A compound of formula (I), or a pharmaceutically acceptable salt thereof,

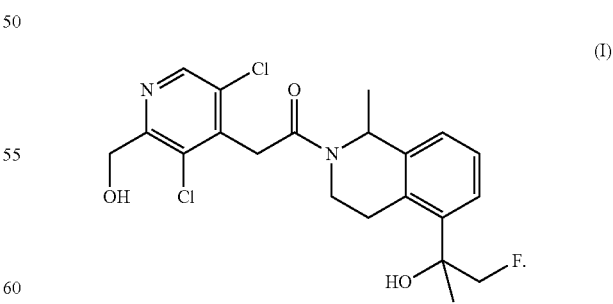

2. A compound of formula (I) according to claim 1, which is 2-[3,5-dichloro-2-(hydroxymethyl)-4-pyridyl]-1-[(1S)-5-[(1S)-2-fluoro-1-hydroxy-1-methyl-ethyl]-1-methyl-3,4-dihydro-1H-isoquinolin-2-yl]ethanone and is represented by formula (IA)

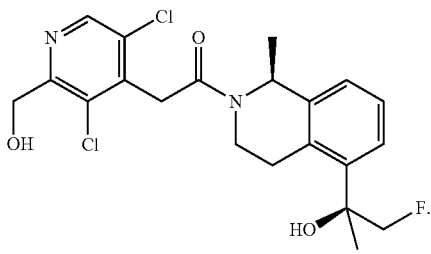

(IA)

3. A compound of formula (I) according to claim 1, or a pharmaceutically acceptable salt thereof, for use in therapy.

4. A pharmaceutical composition comprising a compound of formula (I) as defined in claim 1, or a pharmaceutically acceptable salt thereof, in association with a pharmaceutically acceptable carrier.

5. A pharmaceutical composition comprising a compound of formula (I) as defined in claim 2, or a pharmaceutically acceptable salt thereof, in association with a pharmaceutically acceptable carrier.

6. A method for the treatment of disorders for which the administration of D1 positive allosteric modulator is indicated, which comprises administering to a patient in need of such treatment an effective amount of a compound of formula (I) as defined in claim 1, or a pharmaceutically acceptable salt thereof.

7. A method for the treatment of cognitive and negative symptoms in schizophrenia, cognitive impairment related to neuroleptic therapy, Mild Cognitive impairment (MCI), impulsivity, Attention-Defficit Hyperactivity Disorder (ADHD), Parkinson's disease and other movement disorders, dystonia, Parkinson's dementia, Huntington's disease, dementia with Lewy Body, Alzheimer's disease drug addiction, sleep disorders, apathy, traumatic spinal cord injury or neuropathic pain, which comprises administering to a patient in need of such treatment an effective amount of a compound of formula (I) as defined in claim 1, or a pharmaceutically acceptable salt thereof.

8. A method for the treatment of Parkinson's disease and other movement disorders, Alzheimer's disease, or cognitive and negative symptoms in schizophrenia which comprises administering to a patient in need of such treatment of an effective amount of a compound of formula (I) as defined in claim 1, or a pharmaceutically acceptable salt thereof.

9. A method for the treatment of disorders for which the administration of D1 positive allosteric modulator is indicated, which comprises administering to a patient in need of such treatment an effective amount of a compound of formula (I) as defined in claim 2, or a pharmaceutically acceptable salt thereof.

10. A method for the treatment of cognitive and negative symptoms in schizophrenia, cognitive impairment related to neuroleptic therapy, Mild Cognitive impairment (MCI), impulsivity, Attention-Defficit Hyperactivity Disorder (ADHD), Parkinson's disease and other movement disorders, dystonia, Parkinson's dementia, Huntington's disease, dementia with Lewy Body, Alzheimer's disease drug addiction, sleep disorders, apathy, traumatic spinal cord injury or neuropathic pain, which comprises administering to a patient in need of such treatment an effective amount of a compound of formula (I) as defined in claim 2, or a pharmaceutically acceptable salt thereof.

11. A method for the treatment of Parkinson's disease and other movement disorders, Alzheimer's disease, or cognitive and negative symptoms in schizophrenia which comprises administering to a patient in need of such treatment of an effective amount of a compound of formula (I) as defined in claim 2, or a pharmaceutically acceptable salt thereof.

* * * * *